US012465344B2

(12) United States Patent
Troxell et al.

(10) Patent No.: US 12,465,344 B2

(45) Date of Patent: Nov. 11, 2025

(54) ROBOT-MOUNTED RETRACTOR SYSTEM

(71) Applicant: GLOBUS MEDICAL, INC., Audubon, PA (US)

(72) Inventors: Paden Troxell, Philadelphia, PA (US); Andrew Berkowitz, Santa Clara, CA (US); James Cascarano, Cambridge, MA (US); Stephen Cicchini, North Wales, PA (US)

(73) Assignee: Globus Medical, Inc., Audubon, PA (US)

( * ) Notice: Subject to any disclaimer, the term of this patent is extended or adjusted under 35 U.S.C. 154(b) by 46 days.

(21) Appl. No.: 18/092,325

(22) Filed: Jan. 1, 2023

(65) Prior Publication Data

US 2023/0133876 A1 May 4, 2023

Related U.S. Application Data

(63) Continuation of application No. 17/326,788, filed on May 21, 2021, now Pat. No. 11,540,820, which is a (Continued)

(51) Int. Cl.

*A61B 17/02* (2006.01)
*A61B 34/30* (2016.01)

(Continued)

(52) U.S. Cl.

CPC .......... *A61B 17/0206* (2013.01); *A61B 34/30* (2016.02); *A61B 2017/00017* (2013.01);

(Continued)

(58) Field of Classification Search

CPC ... A61B 17/02; A61B 17/0206; A61B 17/025; A61B 34/30

See application file for complete search history.

(56) References Cited

U.S. PATENT DOCUMENTS

| | | | | |
|---|---|---|---|---|
| 6,804,581 B2 * | 10/2004 | Wang | A61B 34/70 600/101 |
| 8,992,425 B2 * | 3/2015 | Karpowicz | A61B 17/0218 600/233 |

(Continued)

FOREIGN PATENT DOCUMENTS

| | | |
|---|---|---|
| CN | 203315097 U | 12/2013 |
| CN | 107928956 A | 4/2018 |

(Continued)

OTHER PUBLICATIONS

Anonymous: "Fisso Articulated Arm—Scope Holder", Dec. 31, 2018 (Dec. 31, 2018). XP055735979: URL:https://caterhamsurgical.co.uk/index.php/products/fisso-articulated-arm/.

*Primary Examiner* — Eduardo C Robert
*Assistant Examiner* — Steven J Cotroneo

(57) ABSTRACT

A retractor mounting assembly including an end-effector having a body extending between first and second faces. The first face is configured for attachment to an interface plate on the robotic arm of a surgical robot. The second face defines an arm mount. An arm extending between first and second ends with the first end configured for attachment to the end-effector arm mount and the second end providing a retractor mount configured for supportive attachment of a retractor.

10 Claims, 6 Drawing Sheets

Related U.S. Application Data continuation of application No. 16/416,323, filed on May 20, 2019, now Pat. No. 11,045,179.

(51) Int. Cl.
*A61B 17/00* (2006.01)
*A61F 2/46* (2006.01)

(52) U.S. Cl.
CPC . *A61B 2017/0256* (2013.01); *A61B 2034/303* (2016.02); *A61F 2/4611* (2013.01)

(56) References Cited

U.S. PATENT DOCUMENTS

| | | | | |
|---|---|---|---|---|
| 10,646,291 | B2 * | 5/2020 | Turner | A61B 34/37 |
| 11,045,179 | B2 * | 6/2021 | Troxell | A61B 17/0206 |
| 11,317,978 | B2 * | 5/2022 | Cameron | A61B 34/10 |
| 2003/0181800 | A1 * | 9/2003 | Bonutti | A61B 17/8858 600/407 |
| 2013/0023735 | A1 | 1/2013 | Brown et al. | |
| 2013/0193188 | A1 * | 8/2013 | Shelton, IV | A61B 17/07207 227/175.2 |
| 2014/0005679 | A1 * | 1/2014 | Shelton, IV | A61B 17/072 606/130 |
| 2017/0112577 | A1 * | 4/2017 | Bonutti | A61B 90/361 |
| 2017/0273679 | A1 * | 9/2017 | Karpowicz | A61B 1/32 |
| 2017/0360521 | A1 * | 12/2017 | Johnson | A61B 34/30 |
| 2018/0132839 | A1 * | 5/2018 | Friedrich | A61B 17/0206 |
| 2018/0252940 | A1 | 9/2018 | Rabut et al. | |
| 2018/0344426 | A1 | 12/2018 | Bailey et al. | |

FOREIGN PATENT DOCUMENTS

| | | | |
|---|---|---|---|
| CN | 108904208 | A | 11/2018 |
| JP | 2019-22658 | A | 2/2014 |
| WO | 2018/054729 | A1 | 3/2018 |

* cited by examiner

ROBOT-MOUNTED RETRACTOR SYSTEM

CROSS REFERENCE TO RELATED APPLICATIONS

The present application is a continuation of U.S. patent application Ser. No. 17/326,788, filed May 21, 2021, which is a continuation of U.S. patent application Ser. No. 16/416,323 filed on a May 20, 2019, all of which are incorporated in their entirety herein.

FIELD

This disclosure generally relates to devices and methods that improve surgical procedures by, for example, providing a working space for the procedure and improving the surgical conditions for the practitioner of a procedure.

BACKGROUND

In surgical procedures generally, surgeons try to keep incisions as small as possible to minimize or reduce trauma to the patient and damage to tissue. However, it is usually necessary that the surgeon have a clear view of the operating field. Also, an opening may need to be enlarged to accommodate the passing of medical implants therethrough.

In the field of spine surgery, there is an increasing interest in developing minimally invasive methods, as opposed to conventional "open" spine surgery. The goals of these less invasive alternatives are to avoid the surgical exposure, dissection, and retraction of muscles and tissues that is necessary with "open" surgery. In general, a minimally invasive spine surgery system should be able to perform the same procedure as the traditional open technique, but through smaller incisions. As a result, some physicians feel that using a minimally invasive spine surgery system generally causes less soft tissue damage, reduces blood loss and reduces recovery time. In addition, patients generally prefer the smaller scars that are left using a minimally invasive approach.

A variety of retractors are available for use in surgical operations to reposition muscular tissue, vessels, nerves, and other tissue with the aid of retractor blades, thereby providing access to the site of the operation. U.S. Pat. Nos. 9,993,239 and 10,039,539 describe exemplary retractors, each of which is incorporated herein by reference. Surgical retractors are particularly important in performing surgical procedures that involve the spinal column, where access to the surgical site can be obtained through a posterior, anterior, lateral, or combined approach.

Referring to FIG. 1, a prior art retractor system 10 according to the invention is shown. The retractor system 10 includes a retractor 11 having a frame 12 that is attachable to an arm 14. Arm 14 may be attached to a supporting structure 15 which typically includes the patient table. Relative motion between the retractor or port and anatomy is minimized as the patient is also typically immobilized relative to the table. A rigid setup protects the patient from potentially harmful damage caused by shifted retractor blades and a misaligned working corridor.

Several issues commonly arise when fixing the retractor or port with a traditional table-mounted articulating arm. The sterile arm must be mounted to the table frame, which is located beneath the sterile field. Currently, surgical staff must reach below the sterile field to install the arm then return to the sterile field to fix the arm to the retractor or port. The sterile field may also be compromised if the table-arm connection requires intraoperative adjustment. This often occurs because the arm is not properly installed or is rigidly fixed to a non-stiff or loose component of the bed frame. In summary, this method is time consuming which reduces surgical efficiency and patient safety.

SUMMARY

In at least one embodiment, the present disclosure provides a retractor mounting assembly including an end-effector having a body extending between first and second faces. The first face is configured for attachment to an interface plate on the robotic arm of a surgical robot. The second face defines an arm mount. An arm extending between first and second ends with the first end configured for attachment to the end-effector arm mount and the second end providing a retractor mount configured for supportive attachment of a retractor.

In at least one embodiment, the present disclosure provides a retractor mounting system including a surgical robot having a robotic arm defining an interface plate and a retractor mounting assembly. The retractor mounting assembly includes an end-effector having a body extending between first and second faces. The first face is configured for attachment to an interface plate on the robotic arm of a surgical robot. The second face defines an arm mount. An arm extending between first and second ends with the first end configured for attachment to the end-effector arm mount and the second end providing a retractor mount configured for supportive attachment of a retractor.

In at least one embodiment, the present disclosure provides a method of implanting an implant utilizing a retractor mounting system including a surgical robot having a robotic arm defining an interface plate; and a retractor mounting assembly including: an end-effector having a body extending between first and second faces, the first face configured for attachment to the interface plate, and the second face defining an arm mount; and an arm extending between first and second ends, the first end configured for attachment to the end-effector arm mount and the second end providing a retractor mount, the method includes: attaching a retractor to the retractor mount; moving the robot arm and the arm to position and support the retractor at a desired location; actuating the retractor to create a surgical port; and implanting the implant through the surgical port utilizing a surgical tool.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings.

DETAILED DESCRIPTION

Figure 1:
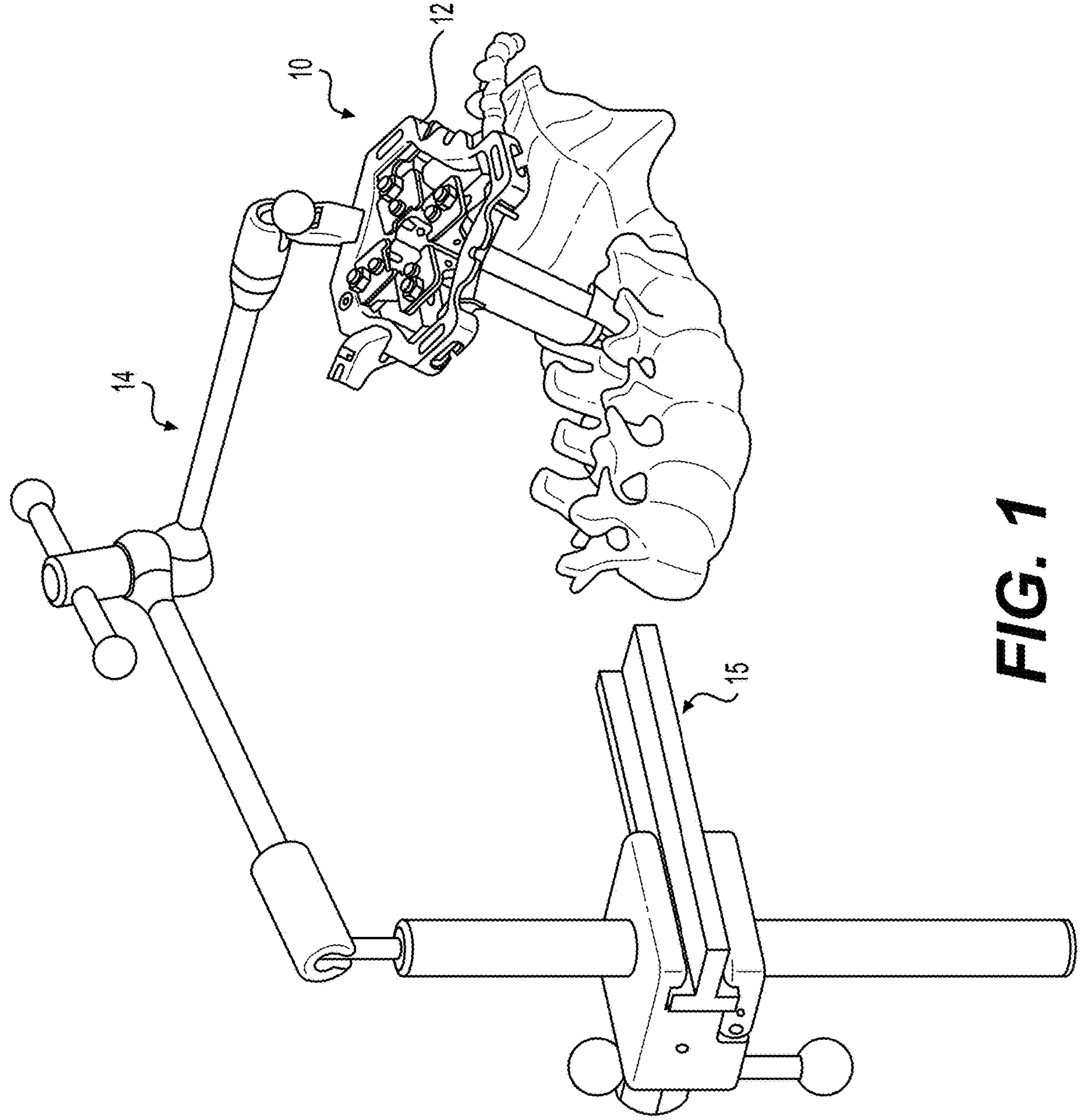
FIG. 1 is a perspective view of a prior art retractor system positioned adjacent a bone model by a surgical arm.

In the drawings, like numerals indicate like elements throughout. Certain terminology is used herein for convenience only and is not to be taken as a limitation on the present invention. The following describes preferred embodiments of the present invention. However, it should be understood, based on this disclosure, that the invention is not limited by the preferred embodiments described herein.

Referring to FIGS. 2-5, an exemplary embodiment of a retractor mounting assembly 100 in accordance with an embodiment of the disclosure will be described. The retractor mounting assembly 100 is configured to rigidly attach to a robotic arm 58 at one end and to a retractor 11 or port on the other end. The retractor 11 generally includes a plurality of blades 14 supported by a frame 12. An attachment member 16 extends from the frame 12 and is configured for attachment with the retractor mounting assembly 100, as will be described in more detail hereinafter. U.S. Pat. Nos. 9,993,239 and 10,039,539 each describe exemplary retractors which may be utilized with the retractor mounting assembly, however, the disclosure is not limited to such designs and various other retractor designs may be utilized.

Figures 5, 5A:
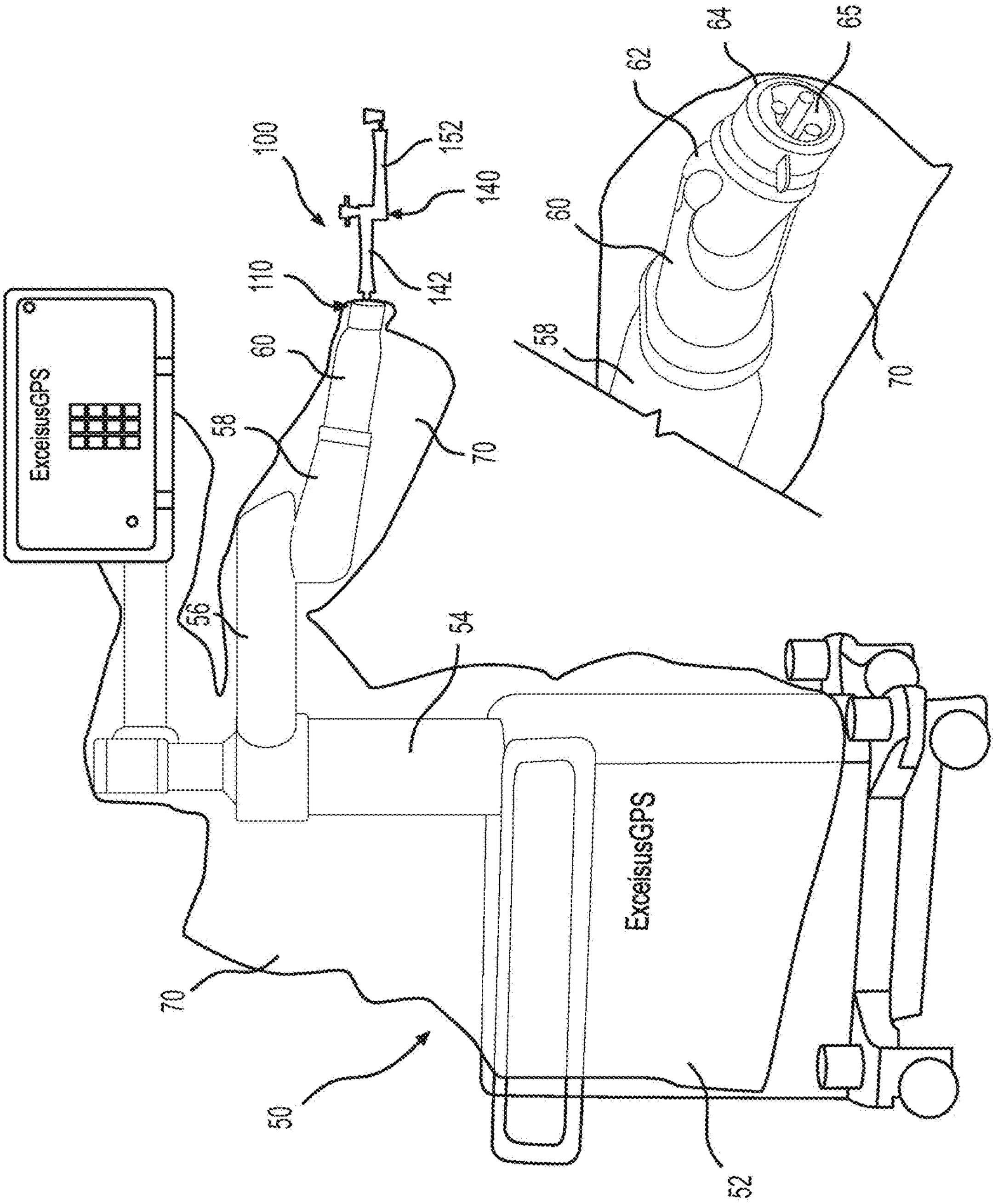
FIG. 5 illustrates the retractor mounting assembly of FIG. 3 mounted on a robot arm with the robot components covered in a sterile drape.
FIG. 5A illustrates the robot arm prior to mounting of the retractor mounting assembly thereon.

An exemplary robot 50 with which the retractor mounting assembly 100 may be utilized will be described with reference to FIGS. 2 and 5. The robot 50 includes a robotic base station 52 which is the main control center for the robotic computer system. The robotic base station 52 supports a vertical column 54 which in turn supports an upper arm 56 connected to a lower arm 58. The lower arm 58 includes an extending portion 60 with a pivot portion 62 pivotally supported relative thereto. The free end of the pivot portion 62 may have a bracelet 64 thereon configured to facilitate manual movement of the arm. The bracelet and/or pivot portion define an interface plate 65 for an end effector 110 of the retractor mounting assembly 100. The robot is configured to facilitate motion about at least 5 axes, namely, vertical 51, shoulder 53, elbow 55, roll 57 and pitch 59. The robot 50 may include other components, for example, a monitor a tablet compartment, a control panel, a connector panel, stabilizers and rolling casters. The operation and function of exemplary robots are described in more detail in US Appln. Pub. Nos. 2017/0258535 and 2019/0021795, which are incorporated herein by reference. The invention is not limited to the specific robot systems described therein and robot systems having various configurations may be utilized.

Figure 3:
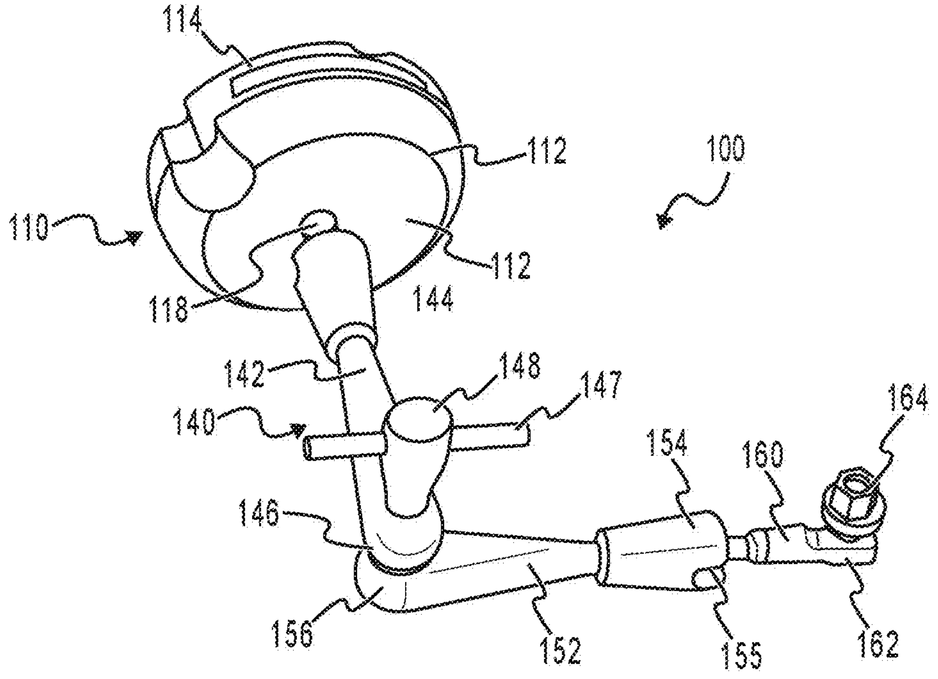
FIG. 3 is a front perspective view of a retractor mounting assembly in accordance with an embodiment of the disclosure.
Figure 4:
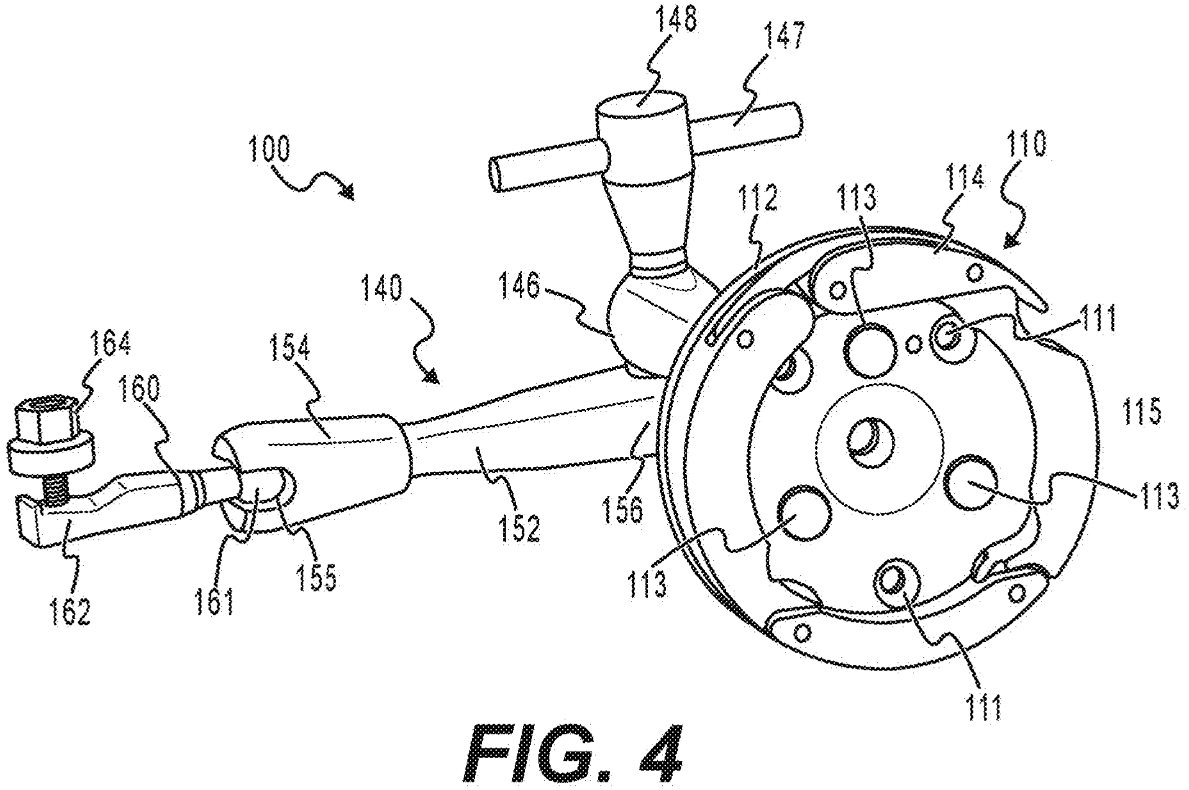
FIG. 4 is a rear perspective view of the retractor mounting assembly of FIG. 3.

Referring to FIGS. 3 and 4, a retractor mounting assembly 100 in accordance with the disclosure will be described. The retractor mounting assembly 100 generally includes an end-effector 110 configured for mounting to the robot arm 58 and an articulating arm 140. The end-effector 110 includes a body 112 with a rear face 115 and a front face 116. In the illustrated embodiment, the rear face 115 includes a series of detents 111 and projections 113 configured to align with and engage corresponding features on the interface plate 65 of the robot arm 58. The body 112 and/or the interface plate 65 may include magnets such that a magnetic assist helps to position and self-align the end-effector 110 on the robot arm 58. The end-effector 110 is equipped with a drape-friendly clamp 114 that allows it to be clamped over the drape 70 covering the robot arm 58 (see FIG. 5A) without damaging the drape 70. The end-effector body 112 is positioned against the interface plate 65 and the clamp 114 is pressed down to lock into place. With this configuration, the end-effector 110, and thereby the retractor mounting assembly 100, may be mounted onto the sterile draped robot 50 (see FIG. 5) without disturbing the sterile field.

The articulating arm 140 includes a pair of arms 142, 152 which are pivotally connected to one another at pivot ends 146, 156, respectively, via an adjustment screw 148. The adjustment screw 148 may include a handle 147 or the like. The free end 144 of the arm 142 includes a mounting member 144 configured for mounting on the front face 116 of the end-effector 110. In the illustrated embodiment, a mounting post 118 extends from the front face 116 and the mounting member 144 includes a slot 145 configured to receive and retain the post 118 (see FIG. 2). While a post and slot configuration is illustrated, the disclosure is not limited to such and other connection assemblies may be utilized. The free end 154 of the arm 152 includes a mounting member 154 configured for mounting a retractor mounting component 160. In the illustrated embodiment, the retractor mounting component 160 includes a ball 161 at one end configured to be received in a slot 155 of the mounting member 154. The opposite end of the retractor mounting component defines a mounting platform 162 which supports a mounting screw 164. The mounting platform 162 and mounting screw 164 are configured to engage the attachment member 16 on the retractor 11. The retractor mounting component 160 is not limited to the illustrated embodiment and may have other configurations which complement the configuration of the attachment member 16 of a given retractor. Relative motion between the robotic arm 58 and retractor 11 or port is rigidly locked by tightening the adjustment screw 148 on the articulating arm 140. Relative motion may be restored intraoperatively to make minor adjustments by loosening the adjustment screw 148. The use of the retractor mounting assembly 100 reduces the potential for compromising the sterile field, provides a quick and easy setup, positions the arm in a convenient location, provides a rigid fixation, and increases intraoperative efficiency.

Figure 2:
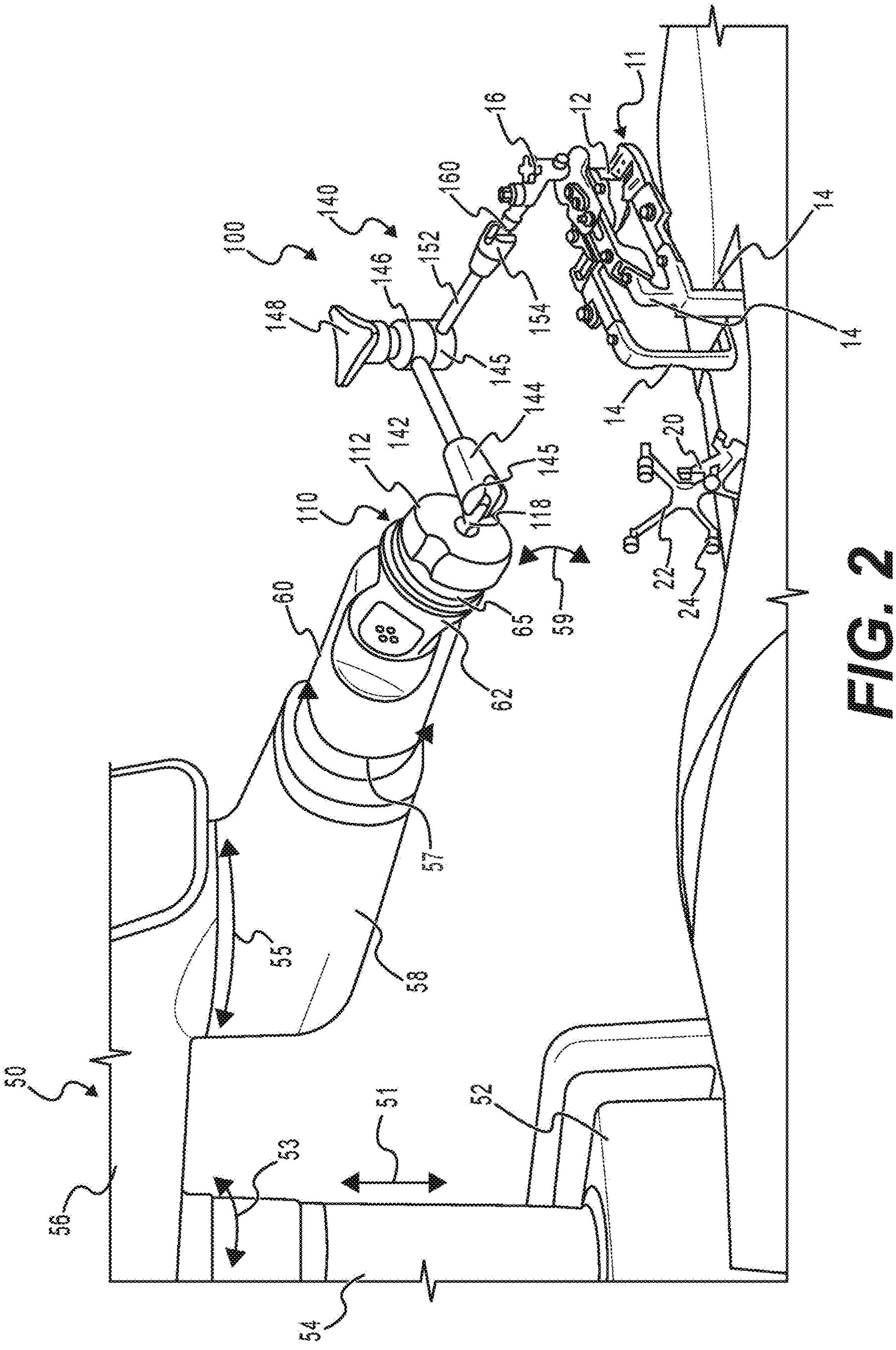
FIG. 2 is a perspective view of one embodiment of a retractor mounting assembly according to the present disclosure mounted on a robot arm and supporting a retractor adjacent a patient.

Referring to FIG. 2, once the retractor 11 is positioned via the retractor mounting assembly 100, the retractor 11 may be actuated to open a surgical port. The surgeon may then use one or more surgical tools 20 as the procedure may require. In one embodiment, the surgical tool 20 is a dynamic reference base used for registering a patient in an imaging space. In another embodiment, the surgical tool 20 may be utilized to implant an intervertebral implant through the surgical port. Since the robot arm 58 is utilized to mount the retractor 11 via the mounting assembly 100, the features of the robot 50 may be utilized during the procedure. For example, the surgical tool 20 may have a tracker 22 with a plurality of markers 24 thereon which can be detected by the robot system and thereby guide the surgeon.

In some instances, there may be a risk that the robotic arm 58 may inadvertently move intraoperatively and potentially cause adverse effects to the patient. To reduce the likelihood of such inadvertent movement, the system may include a lockout device to prevent movement of the robotic arm 58 once the retractor mounting assembly 100 is positioned. This lockout may occur through various means including mechanical locks, disruption of electrical supply, or signal transfer. Such lockout device may be activated through various mechanisms. As one example, the robot 50 may include a user input that activates the lockout feature whereby the user presses a button on the control panel or the like once the retractor mounting assembly 100 is positioned. Upon receipt of such user input, the robot is configured to actuate the lockout through the mechanical lock, disruption of electrical supply, signal transfer or the like. As an another alternative, the end-effector 110 may include a mechanical actuator. For example, upon mounting of the end-effector 110, a portion thereof contacts a mechanical actuator on the robot arm, thereby causing actuation of the lockout.

Figure 6:
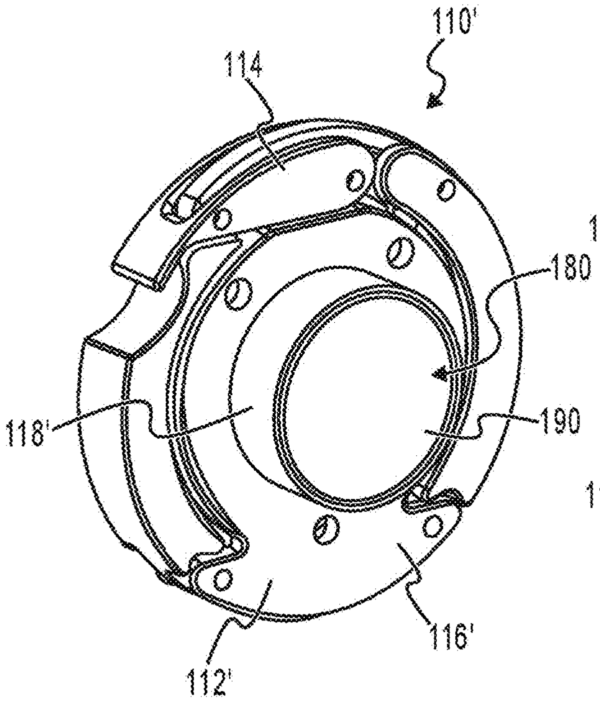
FIGS. 6 and 7 are front and rear perspective view, respectively, of an end-effector in accordance with another embodiment of the disclosure.
Figure 7:
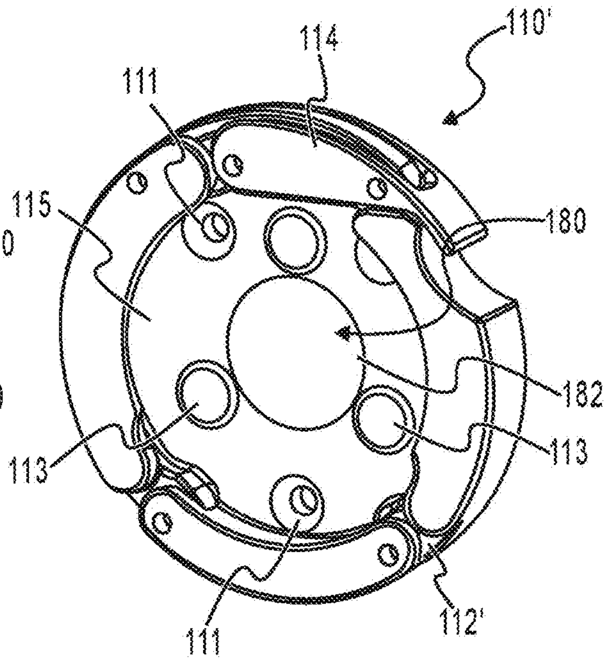
Figure 8:
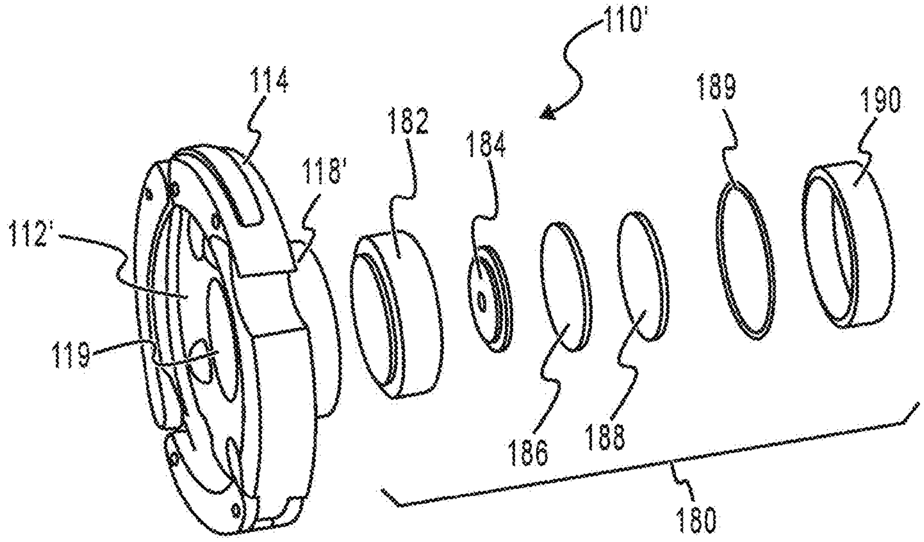
FIG. 8 is an exploded perspective view of the end-effector of FIGS. 6 and 7.

As yet another example, a lockout actuator 180 may be embedded in the end-effector 110, to actuate the lockout device when the articulating arm is attached. An illustrative example of such an actuator 180 within the end-effector 110' will be described with reference to FIGS. 6-8. The end-effector 110' again includes a body 112' with a rear face 115 and a front face 116'. A clamping mechanism 114 is again provided along the body 112' such that the end-effector 110' may be clamped to the robot arm in a manner discussed above.

In the present embodiment, the mounting post 118' defines a hollow chamber 119 configured to house the lockout actuator 180. The lockout actuator 180 is positioned within the chamber 119 such that the surface of an end cap 190 thereof is flush with the end of the post 118'. While not illustrated, in the present embodiment, the articulating arm 140 may be temporarily or permanently mounted to the mounting post 118'. As such, when the end-effector 110' is mounted to the robot arm 58, the articulating arm 140 is also mounted to the robot arm 58. At this time, it would then be desirable to actuate the lockout device via the lockout actuator 180.

The lockout actuator 180 may have various configurations. In the embodiment illustrated in FIG. 8, the lockout actuator 180 includes a pair of printed circuit boards 186 and 188 positioned within opposed end caps 182, 190. The end caps 182, 190 are preferably manufactured from a non-conductive material, for example, polyetheretherketone (PEEK). A wireless power transfer coil 184 is also provided within the lockout actuator 180 such that power to the circuit boards 186, 188 may be provided wirelessly from the robotic arm 58. The transfer coil 184 may also be configured to transfer signals between the circuit boards 186, 188 and the robotic arm 58 or separate signal transfer elements may be enclosed within the actuator 180. An elastomeric ring 189 may be provided within the end caps 182, 190 to seal the components therein. Such minimizes the likelihood of fluids or any other contaminates entering the actuator 180, helping to maintain the sterile quality of the end-effector 110'. The circuit boards 186, 188 are configured to wirelessly instruct the robot 50 to actuate the lockout device once the circuit boards 186, 188 receive power. As such, when the end-effector 110' is mounted on the interface plate 65, the wireless power transfer coil 184 receives power from the robot arm 58. The circuit boards 186, 188 are thereby powered and send the actuation signal to the robot 50 to actuate the lockout device.

Figure 9:
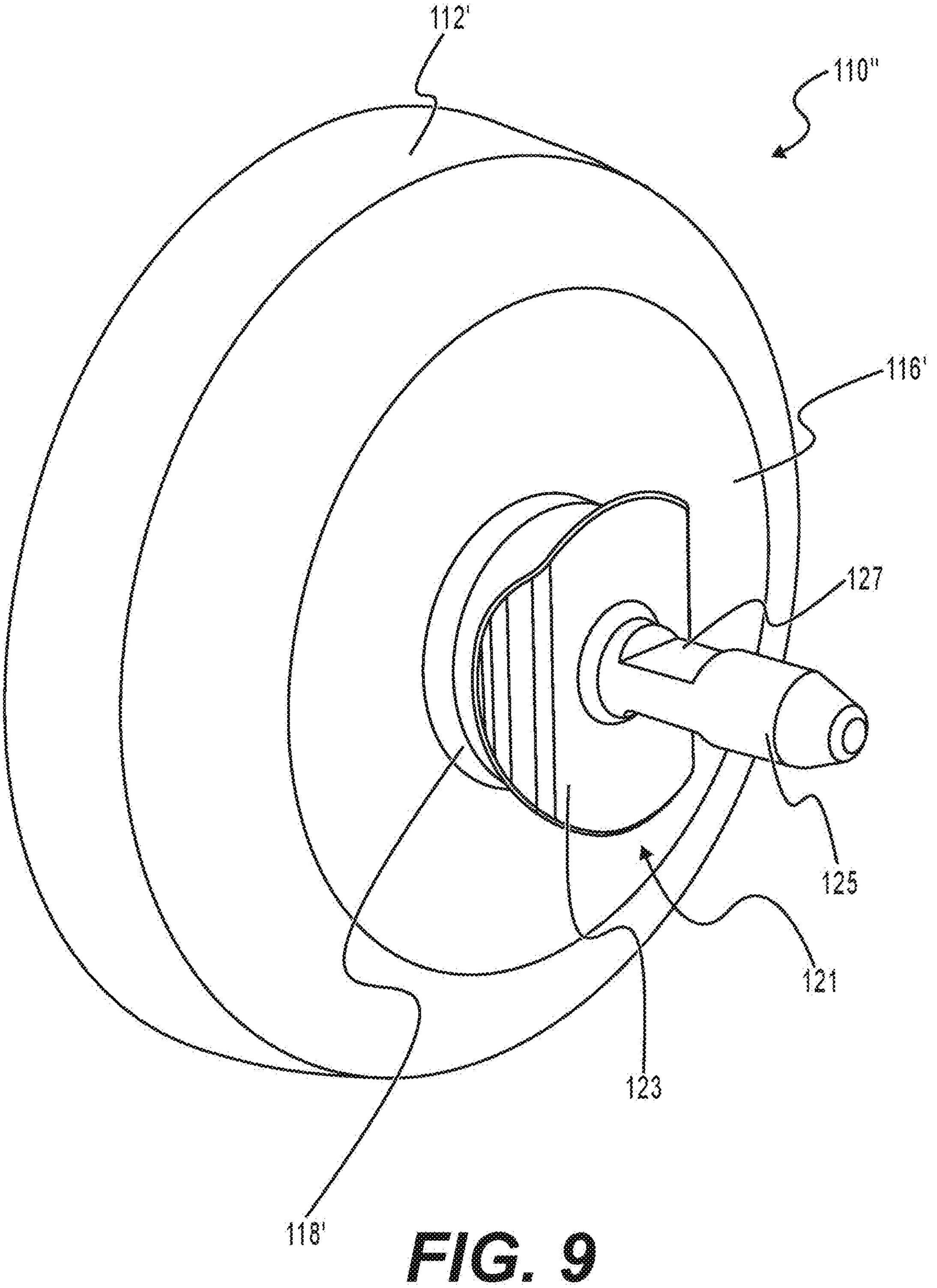
FIG. 9 is a front perspective view of another end-effector in accordance with another embodiment of the disclosure.

In some circumstances, it may be desirable to attach the motion-locking end-effector to the robotic arm 58 apart from the articulating arm 140. This may be due to a change in workflow or to attach an additional accessory that requires total motion lockout. To accommodate these circumstances, another embodiment of an end-effector 110' is shown in FIG. 9. The end-effector 110' is similar to the previous embodiment and includes a lockout actuator (not shown) positioned within the mounting post 118', however, instead of mounting the articulating arm to the mounting post 118', a secondary mounting post assembly 121 is mounted to the mounting post 118'. The secondary mounting post assembly 121 includes a base 123 attached to the mounting post 118'. A secondary post 125 extends from the base 123 and is configured to connect with the articulating arm 140 or other accessories. A locking notch 127 may be provided in the post 125. Since the end-effector 110" includes the lockout actuator, mounting of the end-effector 110", without the articulating arm 140 attached thereto, would still cause actuation of the lockout device. With the robot arm 58 locked in place, the articulating arm 140 or any other accessory may be attached via the secondary post 125.

In another embodiment, the robotic arm may be placed near the surgical site and the motion lock end effector is placed on the robotic arm to lock out motion. The articulating arm is then attached to the motion lock end effector and retractor and tightened to hold the desire position.

In another embodiment, the robotic arm may be placed near the surgical site. The motion lock end effector with articulating arm attached is placed on the robotic arm to lock out motion. The articulating arm is then loosened, attached to the retractor and tightened to hold the desired position.

In yet another embodiment, the articulating arm is loosened and attached to the retractor. The motion lock end effector is then attached to the articulating arm and the robotic arm is placed in reach of the articulating arm and the motion lock end effector is attached. The articulating arm is then tightened to hold the desired position.

It is to be understood that the terminology used herein is for the purpose of describing particular embodiments only and is not intended to be limiting of the invention. Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of this specification and the relevant art and will not be interpreted in an idealized or overly formal sense unless expressly so defined herein.

The terminology used herein is for the purpose of describing particular aspects only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Like reference numbers signify like elements throughout the description of the figures.

The corresponding structures, materials, acts, and equivalents of any means or step plus function elements in the claims below are intended to include any disclosed structure, material, or act for performing the function in combination with other claimed elements as specifically claimed. The description of the present disclosure has been presented for purposes of illustration and description but is not intended to be exhaustive or limited to the disclosure in the form disclosed. Many modifications and variations will be apparent to those of ordinary skill in the art without departing from the scope and spirit of the disclosure. The aspects of the disclosure herein were chosen and described in order to best explain the principles of the disclosure and the practical application, and to enable others of ordinary skill in the art to understand the disclosure with various modifications as are suited to the particular use contemplated.

What is claimed is:

1. A surgical robot having a plurality of end effectors comprising:

a robot including a robot base and a robot arm coupled to the robot base and having a mounting plate at a distal end of the robot arm;

a first end-effector having a clamp for mounting to the mounting plate and adapted to secure a plurality of surgical tools;

a retractor mounting assembly comprising:

a second end-effector having a body extending between first and second faces, the first face configured to attach to the same mounting plate of the robot arm as the first end-effector and the second face defining an arm mount; and an articulating arm comprising a first arm and a second arm, wherein a distal end of the first arm and a proximal end of the second arm are pivotally connected via an adjustment screw, a proximal end of the first arm is configured to connect to the arm mount of the end-effector, and a distal end of the second arm comprises a mounting member comprising a slot configured to receive a ball of a retractor mounting component configured to engage a retractor, a lockout device configured to reduce inadvertent movement of the robotic arm, the lockout device positioned within a hollow chamber of a mounting post such that a surface end cap of the lockout device is flush with the end of the mounting post; and a lockout actuator is configured to actuate the lockout device.

2. The surgical robot of claim 1, wherein the second end-effector is configured to clamp over a sterile drape about the articulating arm without damaging the sterile drape.

3. The surgical robot of claim 1, wherein the first face of the second end-effector includes a plurality of spaced projections configured to align with corresponding features on the mounting plate for aligning the second end-effector with the robot arm mounting plate.

4. The surgical robot of claim 1, wherein the arm mount includes a mounting post extending from the second face.

5. The surgical robot of claim 4, wherein the proximal end of the first arm includes a slot configured to receive and retain the mounting post.

6. The surgical robot of claim 1, wherein the second end-effector includes a bracelet clamp adapted to circumferentially clamp around the mounting plate.

7. The surgical robot of claim 1, wherein:

the second end-effector includes a bracelet clamp adapted to circumferentially clamp around the mounting plate; and the first face of the second end-effector includes a plurality of spaced projections configured to align with corresponding features on the mounting plate for circumferentially aligning the second end-effector with the robot arm mounting plate.

8. The surgical robot of claim 1, wherein the first face includes a clamp configured to clamp the second end-effector to the mounting plate.

9. The surgical robot of claim 1, wherein the retractor mount is defined by a retractor mounting component which is detachable from the second arm.

10. The surgical robot of claim 9, wherein the retractor mounting component complements an attachment member on the retractor.

* * * * *